United States Patent
Nuñez Montalvo

(10) Patent No.: US 10,407,782 B2
(45) Date of Patent: Sep. 10, 2019

(54) APPARATUS FOR THE PRODUCTION OF AN ACID SUPER OXIDATION SOLUTION AND AN ALKALINE SOLUTION WITH INDEPENDENT FLOWS WITH ORP FROM AQUEOUS SOLUTIONS

(71) Applicant: Juan Manuel Nuñez Montalvo, Celaya, Guanajuato (MX)

(72) Inventor: Juan Manuel Nuñez Montalvo, Guanajuato (MX)

(73) Assignee: Juan Manuel Nuñez Montalvo, Guanajuato (MX)

( * ) Notice: Subject to any disclaimer, the term of this patent is extended or adjusted under 35 U.S.C. 154(b) by 0 days.

(21) Appl. No.: 15/610,973

(22) Filed: Jun. 1, 2017

(65) Prior Publication Data

US 2017/0268117 A1    Sep. 21, 2017

Related U.S. Application Data

(62) Division of application No. 14/818,844, filed on Aug. 5, 2015, now Pat. No. 9,708,721.

(30) Foreign Application Priority Data

Aug. 8, 2014    (MX) ........................ MXa2014009629

(51) Int. Cl.
*C25B 1/46* (2006.01)
*C25B 9/08* (2006.01)
(Continued)

(52) U.S. Cl.
CPC ................. *C25B 1/46* (2013.01); *A61K 33/14* (2013.01); *A61K 41/0004* (2013.01); *C25B 9/08* (2013.01);
(Continued)

(58) Field of Classification Search
CPC ... C25B 1/46; C25B 9/08; C25B 11/02; C02F 1/4618; C02F 2001/46171;
(Continued)

(56) References Cited

U.S. PATENT DOCUMENTS

| 5,296,107 A * | 3/1994 | Harrison ............... B82Y 30/00 204/263 |
| 5,306,511 A | 4/1994 | Whang |

(Continued)

FOREIGN PATENT DOCUMENTS

MX    2010014429 A    6/2012

OTHER PUBLICATIONS

Office Action dated Nov. 17, 2016 in U.S. Appl. No. 14/818,844, by Nunez Montalvo.

*Primary Examiner* — Ciel P Thomas
(74) *Attorney, Agent, or Firm* — Panitch Schwarze Belisario & Nadel LLP

(57) ABSTRACT

This invention includes an electrolysis chamber and method for producing controlled flow acid electrolyzed water and controlled flow alkaline electrolyzed water with independent flows from aqueous solutions. Its objective is to produce controlled flow acid water with an oxide reduction potential (ORP) between +1100 and +1200 mV and a pH between 1.5 and 2.9 with a stability and shelf life of over a year, and controlled flow alkaline electrolyzed water with a pH between 9.0-11.0 and an ORP between −700 mV to −800 mV with a shelf life of more than a year.

6 Claims, 7 Drawing Sheets

(51) Int. Cl.
 *C25B 11/02* (2006.01)
 *A61K 41/00* (2006.01)
 *A61K 33/14* (2006.01)

(52) U.S. Cl.
 CPC ............ *C25B 11/02* (2013.01); *Y02A 50/473* (2018.01); *Y02A 50/481* (2018.01)

(58) Field of Classification Search
 CPC .......... C02F 2001/46195; A61K 33/14; A61K 41/0005; Y02A 50/473; Y02A 50/481
 See application file for complete search history.

(56) References Cited

U.S. PATENT DOCUMENTS

| | | | |
|---|---|---|---|
| 5,616,221 A * | 4/1997 | Aoki | C02F 1/4618 204/252 |
| 5,783,052 A * | 7/1998 | Bakhir | C02F 1/46109 204/260 |
| 5,849,346 A | 12/1998 | Hornack | |
| 5,914,130 A | 6/1999 | Whang | |
| 6,143,163 A | 11/2000 | Sawamoto et al. | |
| 7,964,068 B2 | 6/2011 | Kitaori et al. | |
| 8,062,500 B2 | 11/2011 | Sumita | |
| 8,298,588 B2 | 10/2012 | Hornack et al. | |
| 8,323,252 B2 | 12/2012 | Alimi et al. | |
| 2009/0314659 A1 * | 12/2009 | Field | A47L 11/4041 205/770 |
| 2012/0168319 A1 * | 7/2012 | Iltsenko | C02F 1/461 205/556 |
| 2013/0330634 A1 * | 12/2013 | Huber | H01M 4/38 429/320 |

* cited by examiner

APPARATUS FOR THE PRODUCTION OF AN ACID SUPER OXIDATION SOLUTION AND AN ALKALINE SOLUTION WITH INDEPENDENT FLOWS WITH ORP FROM AQUEOUS SOLUTIONS

CROSS-REFERENCE TO RELATED APPLICATIONS

This application is a Divisional of U.S. patent application Ser. No. 14/818,844, filed Aug. 5, 2015, the entire disclosure of which is incorporated herein by reference.

BACKGROUND OF THE INVENTION

U.S. Pat. No. 8,062,500 of the inventor Sumita (Tokyo, JP), herein incorporated by reference, for a method and apparatus for producing negative and positive oxidative reductive potential (ORP) water discloses an apparatus that contains an electrolysis unit and has a cell of three compartments that comprehends a cathode chamber, an anode chamber, and a saline solution chamber between the anode and cathode chambers. Two communicating membranes separate the three chambers. The center chamber includes a fluid flow inlet and outlet and contains insulative material that ensures that direct voltage potential does not travel through the chamber. A supply of water flows through the cathode and the anode chambers into the respective sides of the chamber of saline solution. A supply of water flows through the cathode and anode chambers at the respective sides of the saline chamber. Saline solution flows through the center chamber, either by circulating a pre-prepared aqueous solution containing ionic species, or, alternatively, by circulating pure water or an aqueous solution of, e.g., aqueous hydrogen chloride and ammonium hydroxide, over particulate insulative material coated with a solid electrolyte. Electrical current is provided to the communicating membranes separating the chambers, thus causing an electrolytic reaction that produces both oxidative (positive) and reductive (negative) ORP water.

In U.S. Pat. No. 8,062,500 there are three channels. One works as the donator of electrons or protons towards the other two flows, which act as receptors. The two separation nettings between the channels are polarized so that the force of attraction is done over the donating flow of electrons. The electron flow is in the positive direction towards one of the flows and in negative direction towards the other lateral flow.

U.S. Pat. No. 8,323,252, to inventors Alimi et al. (Santa Rosa, Calif.), herein incorporated by reference, for a method of treating skin ulcers using oxidative reductive potential water solution discloses a method of preventing or treating a condition in a patient, which method comprises administering to the patient a therapeutically effective amount of an oxidative reductive potential (ORP) water solution, wherein the solution is stable for at least about 24 hours. This treatment is done with a solution with a pH of around 7.5 with free chlorine residues at a concentration of 15-35 ppm and a stability of barely 24 hours.

U.S. Pat. No. 7,964,068, to Kitaori, et al. in Jun. 21, 2011, herein incorporated by reference, for a membrane-electrode assembly, electrolytic unit using the same, electrolytic water ejecting apparatus, and method of sterilization discloses a membrane-electrode assembly comprising a first electrode having a shape of a rod-form or a cylindrical-form, a strip-form diaphragm covering the periphery of the first electrode, and a second electrode disposed on a surface of the strip-form diaphragm, an electrolytic unit comprising the membrane-electrode assembly, an electrolytic water ejecting apparatus that contains the electrolytic unit, and a method of sterilization using the membrane-electrode assembly. This patent discloses ionized water for wound use, but doesn't mention the stability or the parameters. The system is based on a spiral system that surrounds the electrode, which reduces the surface contact, decreasing the electrolysis potential.

U.S. Pat. No. 8,298,588, herein incorporated by reference, for a dietary supplement containing alkaline electrolyte buffers discloses an improved dietary and/or therapeutic supplement composition comprising a quantity of a dietary and/or therapeutic supplement agent having a pH that upon ingestion with food or a beverage would limit the effectiveness of the agent. A sufficient amount of an alkaline electrolyte additive is also disclosed in combination with the agent to raise the pH of the composition to a level of from about 8 to about 12.5, in order to increase the effectiveness and functional utilization of the agent while the composition is in the person's stomach. The supplement composition is designed to provide for optimum utilization of a dietary and/or therapeutic supplement agent when taken orally with food or a beverage.

U.S. Pat. Nos. 5,306,511 and 5,914,130 to Whang, both herein incorporated by reference, state that elimination of acid residues from the body is much greater through the use of alkaline water and alkaline minerals in the form of sodium and potassium bicarbonate. According to Whang, acid coagulates blood and the accumulated acidic wastes of our bodies clog our capillary vessels and reduce blood circulation near the accumulated waste locations. It is believed that this phenomena is the primary cause of adult diseases such as diabetes, kidney disease, and the like. Additionally, the claims are drawn to a concentrated alkaline booster solution that is to be added to normal drinking water in order to increase the pH value of said drinking water, and a non-liquid substitute.

U.S. Pat. No. 5,849,346 to Homack, herein incorporated by reference, discloses an acid-neutralizing, balanced electrolyte beverage additive which includes an aqueous solution of potassium hydroxide and a mixture of electrolyte ions including sodium, calcium, magnesium, chloride, bicarbonate, phosphate and sulfate. Homack proposes the additive is useful to increase the normally acidic pH of the beverage from a value of 9.5 up to 14.0.

The previously described three patents disclose additives designed for the alkalization of different liquids or beverages through the addition of chemical mixes that change the pH of the substances to alkaline levels. The additives are beneficial for health, but they forget the ORP levels and other physical-chemical characteristics that can be obtained from the electrolysis of water. These characteristics not only benefit health with pH level, but also with other properties like solubility, hydration, and penetration that can be achieved with a smaller molecular structure than the previously described additives, which have 10-12 water molecules.

Mexican patent MX2010014429A by inventor Maria Guadalupe Gordillo Camas, herein incorporated by reference, for a construction of chambers for the ionization or electrolysis with a coaxial system involves an apparatus to do the electrolysis of water and obtain acid or alkaline water, which is said to help sick people cleanse themselves of chemicals and acidity. The apparatus is made up of a platinized titanium tube with spokes and bolts, dielectric material lids, separation netting and a platinized cell. The coaxial system consists of introducing a flow of water and another with a NaCl solution to the chamber, so that in the system they are mixed and pass to the electrolysis chamber. An acid and an alkaline product are obtained. It is mentioned that the tube has spokes to avoid the membrane sticking to the tube.

In the production process disclosed in MX2010014429A it is noted that in the chamber for ionization two fluid flows are introduced to the system, a flow of water and a flow of NaCl solution, both of equal magnitude. Once inside the lids, they are mixed and pass to the electrolysis chamber.

There is a need in the art for an improved electrolysis chamber with a higher ionization capacity and product stability, reducing wear of product materials. The present invention satisfies this long-felt, unsolved need.

BRIEF SUMMARY OF THE INVENTION

One aspect of the invention comprises an electrolysis chamber. The electrolysis chamber generally comprises a hollow cylindrical titanium cell covered in platinum, a smooth titanium cylindrical electrode covered in platinum or ruthenium, two interior lids, a high density polyethylene based separation membrane surrounding the electrode and attached to the interior lids, and two exterior lids.

Another aspect of the invention comprises a method of producing controlled flow electrolyzed acid water and controlled flow electrolyzed alkaline water with the electrolysis chamber. The controlled flow electrolyzed acid water can be used to treat several ailments by direct application, including diabetic foot. The controlled flow electrolyzed alkaline water can be consumed for improved health benefits.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

The invention has the purpose of obtaining acid electrolyzed water from a controlled flow and alkaline electrolyzed water from a controlled flow. The electrolyzed acid water is used in diabetic foot treatment, obtaining unexpected results of healing in patients. The application of alkaline electrolyzed water is used widely in diverse health treatments, for example reduction of sugar levels in the blood.

This invention includes an electrolysis chamber and method for producing controlled flow acid electrolyzed water and controlled flow alkaline electrolyzed water with independent flows from aqueous solutions. Its objective is to produce controlled flow acid water with an oxide reduction potential (ORP) between +1100 and +1200 mV and a pH between 1.5 and 2.9 with a stability and shelf life of over a year, and controlled flow alkaline electrolyzed water with a pH between 9.0-11.0 and an ORP between −700 mV to −800 mV with a shelf life of more than a year.

The electrolysis chamber comprises a parallel-type catalyzing chamber with two separate flows affected by the polarization of metallic layers that surround them. The polarized metallic layers give off ions that go through a layer of separation of fluids so that when exiting the chamber a flow charged with positive ions and another charged with negative ions are obtained.

The invention is made up of the following elements:

Electrolysis Chamber

The electrolysis chamber, also referred to herein as "electrolysis-process chamber," "electrolysis chamber apparatus," "apparatus," or "chamber," comprises various assembled pieces that form the apparatus that permits the electrolysis of water, from which acid electrolyzed water of controlled flow is obtained. By controlling input parameters like volume, voltage and content of solids, the desired properties of output acid electrolyzed water are controlled. The different pieces are designed so that when assembled they produce an electrolytic chamber where the electrolysis occurs.

Figure 2:
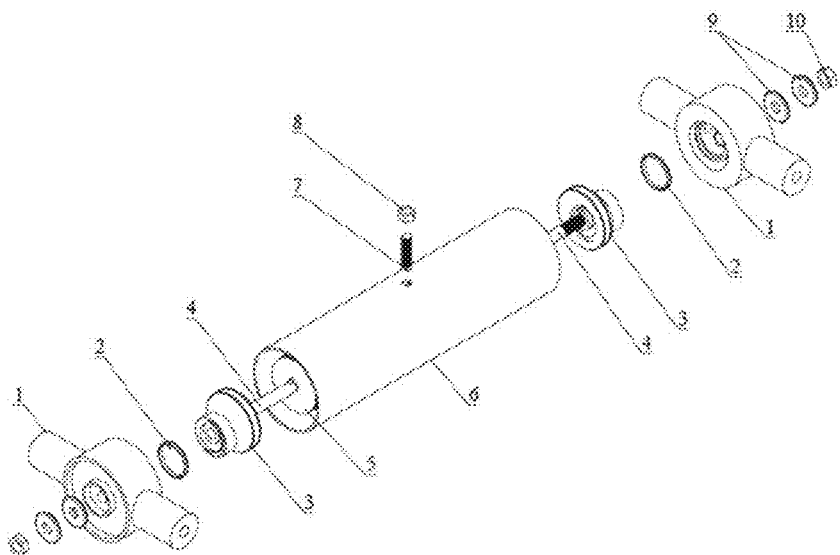
FIG. 2 is an exploded perspective view showing the total components of the apparatus that makes up the electrolysis chamber of FIG. 1, as well as the assembly method.
Figure 5:
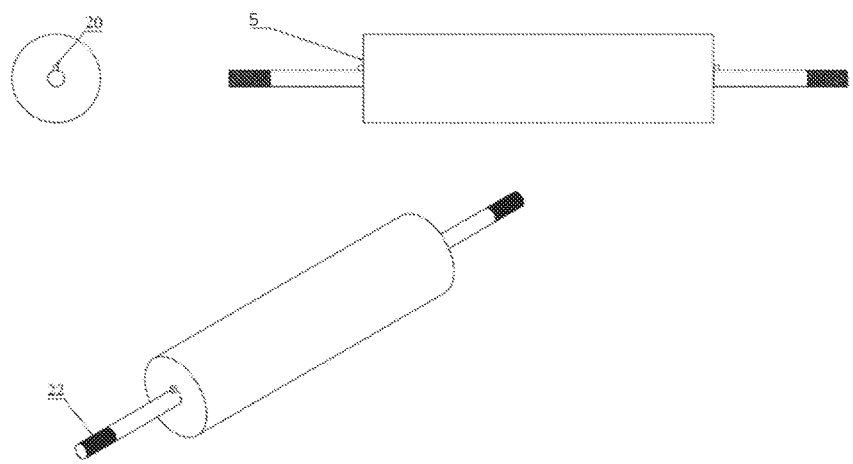
FIG. 5 is a set of end, side and perspective views of the smooth platinum electrode.

As seen in FIG. 2, the parts that make up the electrolytic chamber apparatus are:
1. Upper and lower exterior flow conductor lids
2. Plastic O-ring.
3. Upper and lower interior flow conductor lids
4. Electrode protrusion rod for fastening
5. Electrode
6. Cell
7. Electric contact
8. Fastening nut for electric contact
9. Plastic wrapping and washer for hermetical sealing
10. Fastening screw Parts Description Electrode (5):

A smooth electrode (5) (shown in FIG. 2 and in detail in FIG. 5) is regular and smooth grade 2 titanium cylinder, covered externally with a layer of high conductivity metallic material and having a metallic protrusion rod (4), also referred to herein as "protrusion" or "rod," on each end. One must take into account that a smooth electrode has less surface contact area, so a strong electrolysis is achieved but production of electrolyzed water is a little slower. The metallic rod is welded perpendicularly on its base end to the titanium electrode cylinder, and on the other end has a tip with a screw finish (22) to fit nuts and washers for fastening. The protrusion rods are at a 90° angle with respect to the flat surface that they are attached to, and are concentric with the electrode cylinder. The metallic rod is made up of the same material as the electrode cylinder, and the covering is optional. The electrode covering can be platinum or ruthenium, depending of the type of product desired. If the electrode is covered with platinum, alkaline and acid products can be obtained, while if the covering is based on Ruthenium the electrode will work to obtain acid products only, due to the electric characteristics of Ruthenium. Lastly, the protrusion rods on the near side to the electrode cylinder have a bolt (20) attached that serves as a guide in fastening the flow conductors of the chamber, and for attaching an electrode contact.

Figure 6:
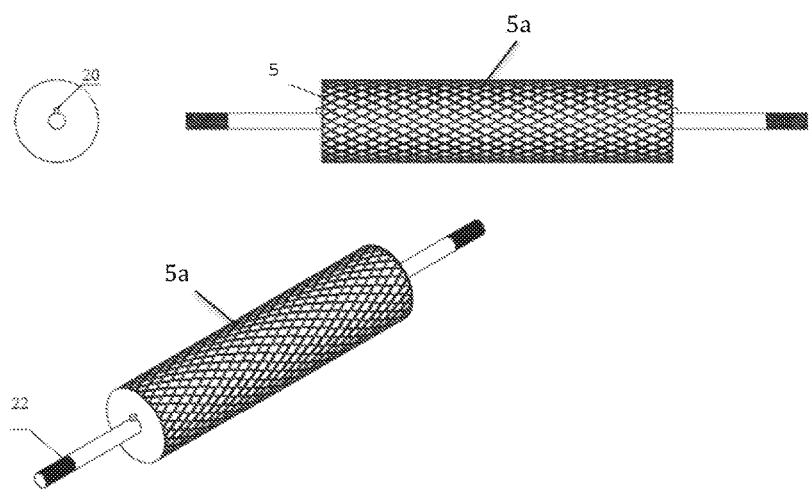
FIG. 6 is a set of views similar to FIG. 5 showing the electrode with netting.

An electrode (5) with netting 5a (shown in FIG. 2, and in detail in FIG. 6) is regular and smooth grade 2 titanium cylinder covered with a caliber 20 netting (5a) of the same material. The netting (5a) covers the exterior of the cylinder with a layer of high conductivity metallic material. The metallic netting (5a) has the purpose of increasing the metal surface contact area for contact with liquid. The upper and lower sides have the same protrusion rods as the smooth electrode with a threaded screw finish (22) and bolt (20), both having the same function as in the smooth electrode. Equally for this type of electrode, Platinum or Ruthenium covering can be used, depending on what is desired to be produced. One must take into account that the netting electrode can process a greater volume of water, for which the speed of production increases, but the electrolysis power decreases slightly. The considerations for the covering are the same as mentioned in the smooth electrode.

Cell (6):

A cell is grade 2 titanium metallic cylinder covered with platinum to have the function of double polarity. The covering should be interior and exterior. The cell's interior diameter is 10-20% greater than the exterior diameter of the electrode cylinder, and its length is in a 5:1 ratio with respect to its diameter. In the central part of the frontal border there is a bolt for fastening the cell contact (7).

Ionic Exchange Separation Membrane (Shown in Detail in FIG. 7):

The ionic exchange separation membrane (24), also referred to herein as "ionic separation membrane," "separation membrane," or "membrane," has a high density polyethylene base interweaved by waved aspersion. It creates a porous layer with an opening of at least one micron and maximum 5 microns. This membrane (24) is very flexible and resistant. When used, cylinders or tubes are formed of a diameter slightly larger than the diameter of the interior lids (3). The membrane's length is equal to the linear distance between one of the ends of the electrode and the end of the protrusion rod at the other end of the electrode.

Figure 3:
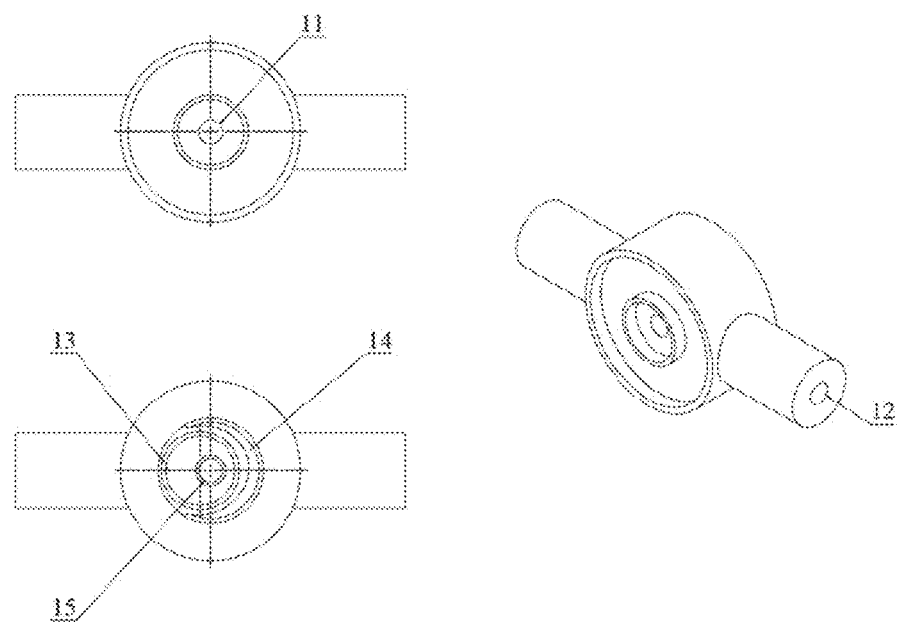
FIG. 3 is a set of diagrams showing an outside face, inside face, and perspective outside views of upper and lower exterior lids.

Exterior Upper and Lower Flow Conductor Lids (Shown in Detail in FIG. 3):

When positioned vertically, the electrolysis chamber has upper and lower ends. The exterior flow conductor lids (1) positioned one each on the upper and lower ends of the assembled chamber, can only be distinguished by the position, since they are the same in form. These lids (1) are made up of FDA Generally Recognized as Safe (GRAS) grade sanitary nitrile. They are cylindrical in shape and have a diameter equal to the cell's diameter. They have two protruding channels (12) arranged at a 180° angle. In the middle of the circle made up by the cylinder, there is a cylindrical opening (11) with a diameter large enough to insert one of the electrode's end rods (4) through this opening. This opening is surrounded by a cylindrical piece of the same material. The piece defines the top where the seal and nuts will be fastened to hold the electrode to the lid (1).

On the exterior flow conductor lid's lower side, there is a border for fastening an external water diffuser to the cell (6). The water diffuser is a mechanical element that distributes water evenly. In the center there is a hole (11) where the rod (4) of the electrode (5) is fastened. This circular hole (11) of sufficient diameter to hold the rod (4) of the electrode (5), is surrounded by a cylindrical piece. Three non-concentric cylindrical pieces are formed from the right side of FIG. 3 and having as a tangent one of the pieces. The first cylindrical piece (14) and closest to the right end, surrounds the lower portion of the lid (1) and its inner diameter surrounds the interior of the lid (1). The second cylindrical piece (13) has an outer diameter which is in a 1:3 ratio with the inner diameter of the first cylindrical piece. The third cylindrical piece (15) has an outer diameter which is the same as the inner diameter of the second piece. The diameter of the third piece is designed to contact the outer diameter of the electrode rod. The channels (12) of the exterior flow conductors connect the two spaces for flow with the exterior, be it for entry or exit according to the flow direction. The channels have a cylindrical shape and pierce the first cylindrical piece in a way that allows the entry and exit of liquid.

Figure 4:
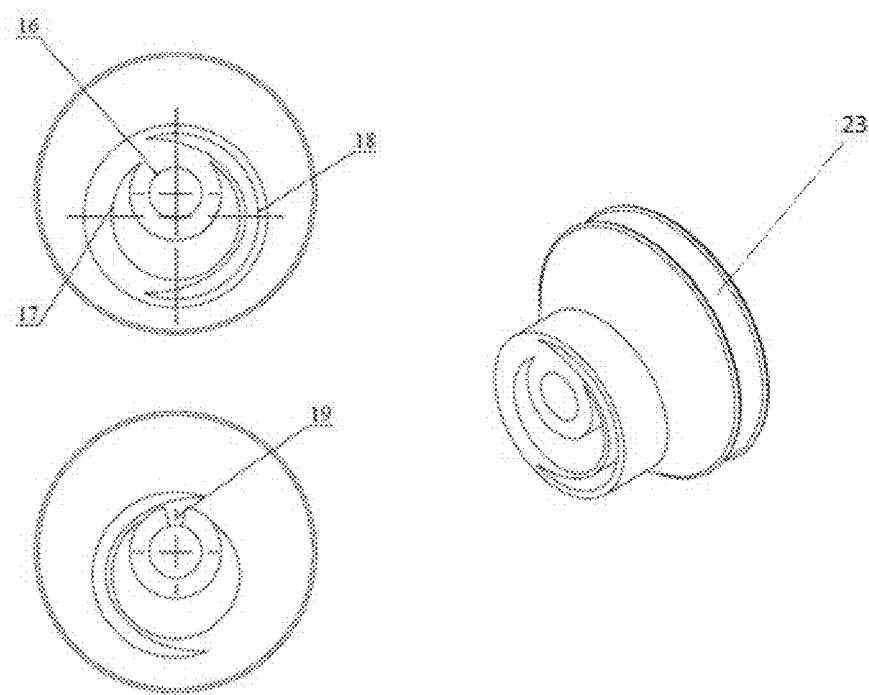
FIG. 4 is a set of diagrams showing outer, inner, and outside perspective views of interior upper and lower lids for the division of the flows.

Interior Flow Conductor Lids (Shown in Detail in FIG. 4).

Similarly to the exterior upper and lower flow conductor lids (1), the electrolysis chamber comprises upper and lower interior flow conductor lids (3), positioned one each adjacent to the upper and lower ends of the assembled chamber.

The upper part of the interior conductor lid (3) is flat on one end and conical towards the other but leans to one side, since it is not concentric in the center (shown in detail in FIG. 4). In the lower part of the conical edge there is a low structure that makes up exterior the border (23) of the lid (3). On this border (23), the ionic separation exchange membrane (24) attaches to the lid (3) through a cloth belt covered with sealing material.

Similarly to the exterior flow conductor, the interior flow conductor lid (3) has an exterior diameter (18) big enough to fasten the external water diffuser by its lower side.

Inside this cylindrical portion there are two holes. The first is the hole (16) to fit one of the rods of the electrode. This hole has the same diameter as the central hole (11) of the exterior lid (1) and is located in the center of the lid, so that when uniting the lids they are aligned. The remaining area covered by the lid's cylindrical portion forms a half moon shape (17) where one of the water flows passes. On the inner side there is an inner cone-shaped water diffuser that reaches the protruding cylinder and fastens the electrode and the half-moon opening. The cylindrical portion is divided at one end (19) of the half-moon, so that the electrode's contact bolt fastens here, perfectly aligning the lids.

Entry and Exit Tubing:

Flexible food grade plastic hose with an outer diameter equal to the inner diameter of the entry and exit conduits (12) of the exterior lids (1).

Assembly of the Electrolysis Chamber

Figure 7:
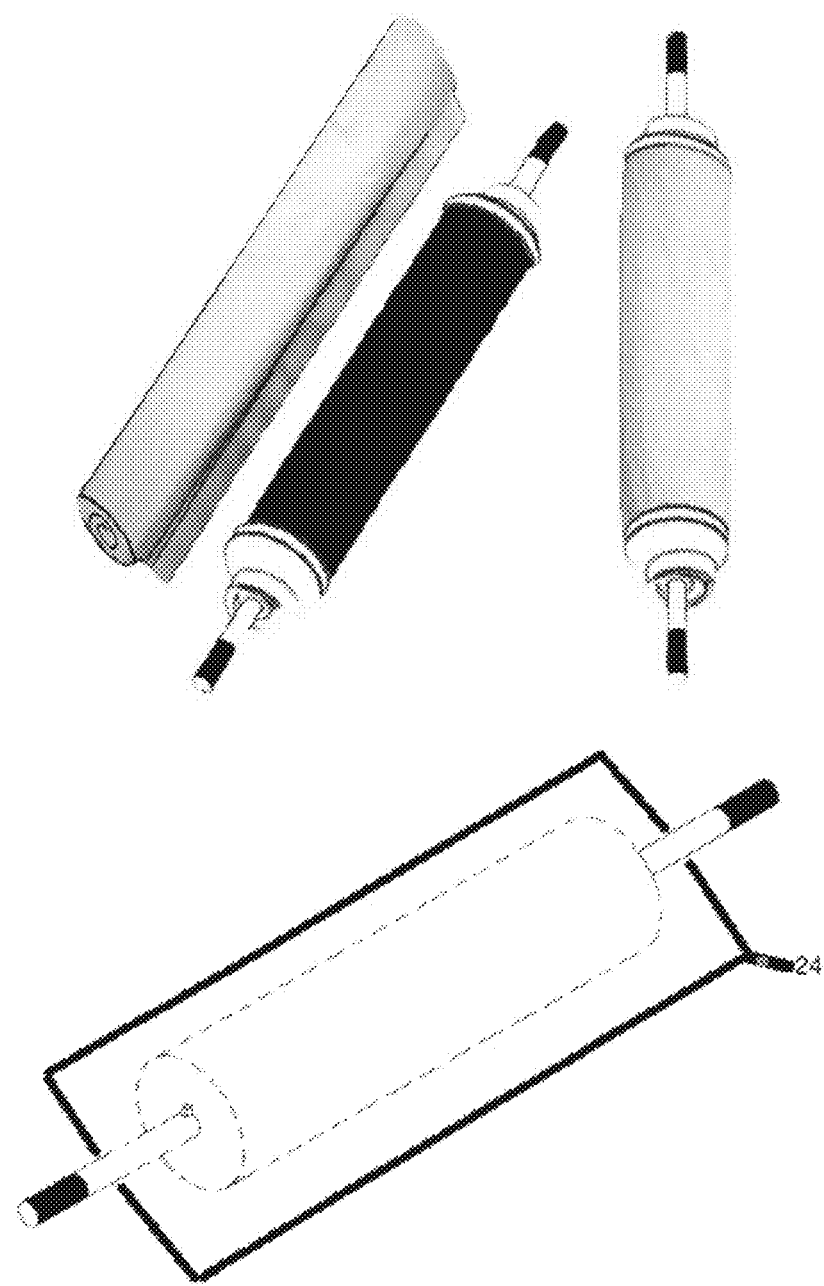
FIG. 7 is a set of photographs and perspective diagrams showing the electrode and ionic separation membrane.

Electrode (5)—Interior Flow Conductor Lid (3)—Ionic Exchange Separation Membrane (24) (See FIG. 7).

1. A conduit is made with the separation membrane (24) in a way that it can contain the electrode (5) lengthwise and widthwise. The separation membrane (24) is generally a little longer than the electrode in order to have a margin for maneuvering the material when assembling.

2. One of the electrode's connection protrusion rods (4) is inserted in the first interior flow conductor lid (3) through the inner side, until the lid reaches the bolt (20) of the electrode. The cylinder protrusion (19) of the interior flow conductor lid is fixed to the bolt (20).

3. The electrode (5) is inserted in the separation membrane (24), and the end of the separation membrane (24) is attached to the previously positioned interior lid. The fastening is done through a nylon belt covered with sealing material over the fastening exterior border (23) of the interior lid (3).

4. The second interior flow conductor lid is positioned on the opposite side of the electrode. It is fastened in the same way as the first interior flow conductor lid onto the bolt (20) of the electrode in a way that it is aligned with the lid at the other end. The electrode is fully covered by fastening the second end of the separation membrane (24) to the fastening exterior border (23), so that the electrode's body is between both internal flow conductor lids and covered by the separation membrane (24), which is fastened to the fastening exterior borders of the interior lids. The half-moon openings of each interior flow conductor lid are positioned with the same orientation.

Electrolysis Chamber

1. An exterior flow conductor lid (1) is fastened to the electrode (5), which is now covered with the separation membrane (24) and the interior flow conductor lids (3), such that when introducing the electrode's protrusion rod (4) in the exterior flow conductor lid (1), the interior flow conductor lid (3) ends up on the lower side of the exterior flow conductor lid. The flow conductors should be positioned such that the half-moon opening (17) in the interior flow conductor fits in the inner half-moon formed on the lower side of the exterior flow conductor. To guarantee a hermetic separation between the flow conductors, a plastic wrapping (O-ring) (2) should be placed in the cylinder that surrounds the connection between interior and exterior flow conductors (on the lower side of the exterior flow conductor lid).

2. The flow conductors are fastened through enforced pressure by a pair of stainless steel metallic washers (9) and a nut (10) that are screwed onto the electrode protrusion (4). The electrode protrusion goes through both sets of flow conductors (3 and 1). Plastic wrappings are used (O-ring) underneath the washers and between the electrode's protrusion and the exterior conductor lid, to avoid liquid leaks in the chamber.

3. The metallic cell (6) is positioned such that the electrode fits inside, and the cell is fastened to the exterior flow conductor (1), which has already been fastened to the electrode (5) and, thus the interior flow conductor (3). This arrangement seals the cell with the exterior flow conductor lid and prevents the exit of fluids from the apparatus through gaps.

4. The remaining exterior flow conductor lid is positioned in the same way as previously described and the cell is fastened to the second exterior flow conductor lid.

5. To connect the electrolysis chamber to an electric current, one of the contacts (7) is positioned at the lateral bolt of the metallic cell, which will be fastened with a pair of washer and screw (8). The second contact is connected at the upper end of electrode, on the protrusion rod (4) bolt, and is equally fastened with a washer and screw.

Figure 1:
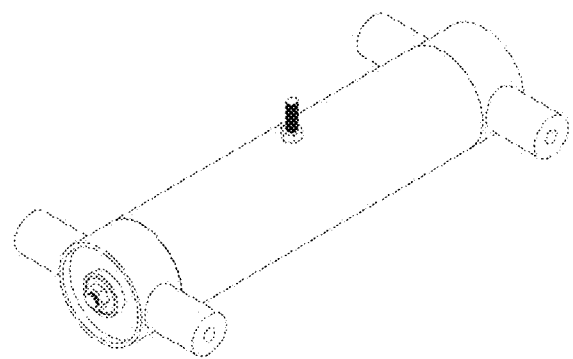
FIG. 1 is a perspective view of the complete assembly of an electrolysis chamber, according to one embodiment of the invention.

The assembled electrolysis chamber apparatus is shown in FIG. 1.

Controlled Flow Electrolyzed Water Production Method

Water Preparation:

1. Common drinking water is filtered through a method that comprises of 2 main phases. Solids with a particle size of 5-10 microns are filtered out, to eliminate some salts and foreign materials. Chlorine, odors and undesired flavors are eliminated with an activated carbon filter. After this step, filtered water should have a low salt concentration, an ORP of +300 mV and a pH close to 7.

2. An additional NaCl USP (United States Pharmacopoeia Grade) aqueous solution is prepared, at a concentration of at least 2% NaCl. The NaCl aqueous solution will be used as an electrolyzing solution, supplied to the main flow in an amount consistent with the required conditions of the end product.

3. To produce controlled flow electrolyzed acid water or controlled flow electrolyzed alkaline water, the electrolysis chamber should be fed with two water flows that have been mixed with the electrolyzing solution. The proportion of electrolyzing solution that is mixed with the main flow will vary depending on the electrolysis conditions desired and external factors that affect it. Therefore, it could vary between 5 to 35 mL of electrolysis solution for every 100 mL of water flow. The flows should be continuous, without air bubbles, and should have a pressure of at least 8 psig when entering the chamber. The maximum pressure will depend on the material of the tubing and connections throughout the chamber.

Water in the Electrolysis Chamber:

1. For the most effective electrolysis, the chamber should be positioned vertically. Otherwise, the flow pressure should be adjusted to obtain the adequate parameters.

2. The electrolysis chamber should be assembled and positioned such that the contact at the lateral bolt of the cell is in the front. The flow conductor lids are positioned such that the entry and exit of a first flow is to the right side, and a second flow to the left.

3. The path of the first flow, or exterior flow, is as follows:

a. The first flow, or exterior flow, enters the chamber by the first channel of the exterior flow conductor, positioned in the lower part of the chamber. The first flow enters the half-moon opening of the exterior flow conductor.

b. The exterior flow conductor half-moon connects to the interior flow conductor half-moon opening. The first flow travels through this opening.

c. Once the first flow has traveled through the interior flow conductor, it lies between the separation membrane and the inner face of the electrolysis cell. The first flow will fill this space through the entire chamber.

d. When arriving at the upper end of the chamber, the first flow meets the other interior flow conductor and rises through its external face, until reaching the other exterior flow conductor in the space that is formed between the second and third nitrile cylindrical pieces.

e. Once there, the first flow goes through the first channel of the upper exterior flow conductor and exits the chamber.

4. The path of the second flow, or interior flow, is as follows:

a. The second flow, or interior flow, passes through the entry to the exterior flow conductor on the left side (i.e., the second channel), and continues to the half-moon interior of the exterior conductor.

b. Then the second flow goes up to the interior flow conductor lid through the interior half-moon opening that forms in its cylindrical part between the exterior flow conductor and the interior flow conductor. This half-moon goes through the conductors and reaches the electrode.

c. The flow goes up uniformly around the electrode, but is contained by the separation membrane.

d. When reaching the upper part of the electrode, the second flow is guided through the corresponding cone of the interior flow conductor, to the half-moon that will guide it to the exterior flow conductor and channel it to its exit.

e. Once there, the pressurized liquid exits the chamber through the second channel of the upper exterior flow conductor.

5. Both flows are generated by pressure and should be continuous.

6. The work conditions are the following:

a. The entry water should not have odor or taste, and all chlorine content should be removed.

b. The electrolysis chamber should be perfectly sealed and should not have leaks.

i. Hermetic seal, through an O-ring at the contact point between the flow conductors and the metallic cell.

ii. Pressured sealing in the fastening of the membrane to the interior flow conductors.

iii. Pressured sealing at the contact point between the of the interior and exterior flow conductors and each one of the ends of the electrolysis chamber apparatus.

EXAMPLES

Electrolysis Chamber Operation

In order to make controlled flow electrolyzed acid water with the electrolytic chamber, certain characteristics of the materials used are required.

1. The metallic cell should not have any leaks or breakages, and the platinum covering should be complete and uniform along the entire piece.

2. The exterior and interior nitrile flow conductors should not have fissures, and their contours should be visible and adequate for the connection of both sets of conductors to the other parts.

3. The separation membrane should not have fissures or breakages, and must be perfectly fastened and sealed to the interior lids. For best results, the material of the separation membrane should be permeated for 6 or 7 hours with water flow with a pressure similar to working conditions, enabling a more efficient ionic exchange. In one embodiment, the separation membrane can be a propylene canvas.

4. The entire surface of the electrode should be free of cavities, and the complete covering should be free of splinters. For the acid product, a ruthenium covered smooth electrode will be used to improve the potency of the end product.

5. The chamber should be correctly connected to the contacts that will apply the electric current.

6. A continuous flow of filtered water and NaCl solution should be guaranteed.

Fabrication Method

1. Before the filtered water enters the electrolysis chamber, it is made to flow with a pressure of approximately 20 lb. To this flow the NaCla solution is added in a proportion of 5:100 to 35:100. The pressure will vary according to the requirements of the exit product and external manufacturing conditions.

2. The water flow and electrolyzing solution, previously mixed, are divided in two equal flows (first and second flows), with an approximate pressure of 10 lb, which enter the chamber in its lower part. The first flow enters by the first channel and travels the path previously mentioned, while the second flow enters by the second channel to its corresponding path.

3. Once the flows are running through the chamber, they are calibrated so that the negative flow (first flow) is greater in a 5:1 ratio than the positive flow (second flow). This is done by reducing the area of the exit channels until achieving the required proportions, while maintaining the exit volumes of water stable.

4. The electrode and the cell are polarized by application of direct current through the electrode and cell contacts, making the electrode negative (cathode) and the cell positive (anode). The power will vary according to the required exit parameters and conditions such as temperature, solid content and water pressure. Such energy or polarization power should be controllable.

5. The first flow remains between the cell and the membrane of ionic exchange, so that it will be in contact with the anode. On the other hand, the second flow is in contact with the cathode during its passage through the chamber.

6. When the first flow enters the chamber and contacts the positive pole, it attracts the negative side of the water molecule, in this case $OH^-$. In the opposite case, the second flow would be attracting the positive pole, or $H^+$.

7. The first flow will also be affected by the cathode, so that during its travel the molecule will separate into $H^+$ and $OH^-$. The $OH^-$ will remain in the first flow, while the $H^+$ passes through the separation membrane to the second flow. The same effect happens to the second flow, but in the opposite direction. The second flow keeps the $H^+$ and gives away the $OH^-$ to the first flow through the separation membrane.

8. The ion exchange rate will depend on the power applied to the cell and electrode, the rate of NaCl solution added, and the flow speed.

9. The quantity of product obtained will depend mainly on the chamber proportions, and additionally on the work conditions.

10. As a result, the second flow is an acidic solution (pH 1.5-3.0), with a high ORP (1000-1200 mV), without free residual chlorine, with a high content of chlorides (1600 mg/L), and other physicochemical characteristics, making it a good disinfectant for many uses in different markets. While the first flow is an alkaline product with a high pH (10-13), a negative ORP (−800 to −900 mV), and other characteristics. In order to obtain an adequate alkaline product for consumption, modifications to the method should be made (electrode and work conditions).

11. In order to obtain an alkaline solution, the electrode can be smooth or with netting, depending on the volume that is desired. There will be a greater volume when using the electrode with netting. The covering should be strictly platinum, which will guarantee the product is suitable for consumption.

12. In this example the polarity of the cell and the electrode can be maintained like cathode and anode, respectively, but can also be reversed due to the double electrical capacity of platinum. The results obtained in the first and second flows will depend on this polarization.

13. The entry volume to the chamber through the first and second flows should have a 3:1 ratio, where the greater volume is the alkaline solution that will be obtained with a pH of 9-11, an ORP of between −750 to −800 mV, and physicochemical characteristics that make it adequate for consumption and give it all of its strong qualities for use in healthcare. The acid flow that is obtained from this method also has bactericide characteristics, but its parameters are lower than in the previous method, therefore it should be utilized for applications requiring lower potency.

Examples of Use

The controlled flow electrolyzed acid water obtained by the previously described method has antiseptic abilities, since it functions as a bactericide and has an effect on cellular membranes and tissues. The oxide reduction potential (ORP) makes microorganisms lose electrons and their capacity to maintain structure. When absorbing the solution quickly, they swell and blow up. For this reason, electrolyzed acid water is applied on tissues damaged by: ulcerative, infectious and traumatic processes, ambient exposed wounds, etc., where body fluids can be lost. When administering controlled flow electrolyzed acid water, hydrogen bridges are restored, repolarizing tissues and preventing the spread of infection from hyperglycemia and travel of microbiota. In addition, electrolysis improves the acid water's capacity to hydrate cells and tissues, since it contains molecules joined weakly by ionic bridges and having a high dissociation capacity.

Upon contact with tissue, the electrolyzed acid water is distributed homogenously without adversely affecting healthy tissue. It disinfects by modifying bacterial pH, eradicates positive and negative Gram microorganisms, diminishes strong odors and injured or nectrotic tissues, and removes and eliminates oozing and abscesses when used in deep injuries. Necrotic tissue and slough is oxidized, making it easy to remove by degrading the denaturalized fibrin, collagen and elastin. By maintaining the environment humid, it promotes the angiogenesis and growth of tissue, avoids drying, and improves cell hydration. It promotes the appearance of fibroblasts that synthesize collagen and mucopolysaccharides, necessary for tissue repair. Due to these characteristics, controlled flow electrolyzed acid water can be used in the disinfection of wounds of all types with aerobic or anaerobic bacteria. For example, it can be used in treatment of diabetic foot, dry or gaseous gangrene, varicose ulcers, arterials, bed sores, neuropathic conditions, diabetic angiopathy, infected surgical wounds, and dermatological treatments against mycosis, external skin tuberculosis, acne, atopic and fatty dermatitis, athlete's foot on feet and hands, warts, ingrown toenails, and matricectomy. Controlled flow electrolyzed acid water is a cell regenerator and preventor of infections in burns and viral and bacterial surface wounds. It is also a biological sterilizer, for example for use on healing material, surgical instrumentation, operating rooms and medical areas. By modifying the exit parameters of the controlled flow electrolized acid water, it can have a useful application in fields like agriculture and food production, industrial, veterinary and others.

Microbial isolates were exposed to the controlled flow electrolyzed acid water and samples were measured at 10 s, 30 s, 60 s, 3 min, 5 min, and 8 min after exposure for detection of the microbial isolates. Table 1 shows the time at which the microbial isolates were no longer detected (ND). The bactericide characteristics of controlled flow electrolyzed acid water shown in Tables 1 and 2 were tested at the University Center of Exact Sciences and Engineering of the University of Guadalajara, in the Division of Basic Sciences, Department of the Pharmacy, Laboratory of Sanitary Microbiology.

TABLE 1

| REGISTER | STRAIN TESTED | CONCENTRATION (UFC/ml) | 10 sec | 30 sec | 60 sec | 3 min | 5 min | 8 min |
|---|---|---|---|---|---|---|---|---|
| 52014 | Enterobacter aerogenes | $8.4 \times 10^5$ | | | ND | | ND | ND |
| 52014 | Salmonella typhy | $7.6 \times 10^6$ | | ND | ND | ND | | |
| 52014 | Acinetobacter baumannii | $2.6 \times 10^5$ | | ND | ND | ND | | |
| 52014 | Bacillus spp | $1.8 \times 10^6$ | | ND | ND | ND | | |
| 52014 | Klebsiella pneumaniae | $6.8 \times 10^6$ | | ND | ND | ND | | |
| 52084 | Candida albicans | $6.8 \times 10^7$ | ND | ND | ND | | | |
| 52084 | Aspergillus niger | $6.1 \times 10^6$ | ND | ND | ND | | | |
| 52649 | Enterobacter gergoviae | $2.4 \times 10^7$ | ND | ND | ND | | | |
| 52649 | Pseudomona aeruginosa | $2.4 \times 10^8$ | ND | ND | ND | | | |
| 52649 | Salmonella spp | $3.2 \times 10^7$ | ND | ND | ND | | | |
| 52649 | Candida parapsilosis | $3.7 \times 10^5$ | ND | ND | ND | | | |
| 52649 | Lysteria monocytogenes | $1.6 \times 10^7$ | ND | ND | ND | | | |
| 52649 | Enterobacter cloacae | $2.2 \times 10^7$ | ND | ND | ND | | | |
| 52649 | Sthaphylococcus thermophilus | $4.6 \times 10^6$ | ND | ND | ND | | | |
| 52649 | Bacillus cereus | $1.6 \times 10^5$ | ND | ND | ND | | | |
| 52649 | Leuconostc messenteroides | $7.1 \times 10^{10}$ | ND | ND | ND | | | |
| 52649 | Lactococcus lactis | $7.5 \times 10^7$ | ND | ND | ND | | | |
| 52649 | Escherichia coli | $9.1 \times 10^7$ | ND | ND | ND | | | |
| 52649 | Staphilococcus aureus | $1.2 \times 10^7$ | ND | ND | ND | | | |
| 52649 | Raoutella terrigena | $3.9 \times 10^5$ | ND | ND | ND | | | |
| 52649 | Vibrio cholerae | $7.4 \times 10^5$ | ND | ND | ND | | | |
| 52649 | Escherichia coli O157:H7 | $1.3 \times 10^7$ | ND | ND | ND | | | |
| 52649 | Stenotrophomonas maltophilia | $3.5 \times 10^6$ | ND | ND | ND | | | |
| 52649 | Sacccharomyces cereviciae I | $2.7 \times 10^6$ | ND | ND | ND | | | |

Table 1 shows the anti-microbial efficacy in vitro of the controlled flow electrolyzed acid solution.

TABLE 2

PHYSICOCHEMICAL ANALYSIS

| PARAMETER OR CONSTITUENT | VALUE OR CONCENTRATION | MEXICAN NORM OF ANALYSIS | NOM-201-SSA1-2002 (maximum permissible limits) |
|---|---|---|---|
| Color | 1 unit (Pt—Co) | NMX-AA-045-SCFI-2001 | 15 units (Pt—Co) |
| Odor | NA | NOM-041-SSA1-95 | Odorless |
| Flavor | NA | NOM-041-SSA1-95 | Tasteless |
| Turbidity | <1 UTN | NMX-AA-038-SCFI-2001 | 5 U TN |
| Arsenic | <0.002 mg/L | NMX-AA-051-SCFI-2001 | 0.025 mg/L |

TABLE 2-continued

| | | | |
|---|---|---|---|
| Barium | <0.0098 mg/L | NMX-AA-051-SCFI-2001 | 0.700 mg/L |
| Boron | <0.150 mg/L | NMX-AA-051-SCFI-2001 | 0.300 mg/L |
| Cadmium | <0.0048 mg/L | NMX-AA-051-SCFI-2001 | 0.005 mg/L |
| Cyanides | <0.005 mg/L | NMX-AA-058-SCFI-2001 | 0.050 mg/L |
| Free Residual Chlorine | Not detected | NMX-AA-108-SCFI-2001 | 0.100 mg/L |
| Total Chromium | <0.0052 mg/L | NMX-AA-051-SCFI-2001 | 0.050 mg/L |
| Total Coliform Bacteria | Not detectable NMP/100 mL | NMX-AA-042-SCFI-1987 | <1.1N MP/100 mL |
| Nickel | <0.012 mg/L | NMX-AA-051-SCFI-2001 | 0.020 mg/L |
| Silver | <0.007 mg/L | NMX-AA-051-SCFI-2001 | 0.100 mg/L |
| Nitrates | 3.15 mg/L | NMX-AA-79-SCFI-2001 | 10 mg/L |
| Nitrites | <0.010 mg/L | NMX-AA-99-SCFI-2001 | 0.050 mg/L |
| pH | <2.26 units | NMX-AA-008-SCFI-2000 | 6.5-8.5 Units |
| Lead | <0.0052 mg/L | NMX-AA-051-SCFI-2001 | 0.010 mg/L |
| Selenium | <0.002 mg/L | NMX-AA-051-SCFI-2001 | 0.010 mg/L |
| SAAM | <0.230 mg/L | NMX-AA-039-SCFI-2001 | 0.500 mg/L |
| Total Coliforms | Not detectable NMP/10 mL | NMX-AA-073-SCFI-2001 | <1N MP/100 mL |

PARTICULAR CONDITIONS

| PARAMETER OR CONSTITUENT | VALUE OR CONCENTRATION | MEXICAN NORM OF ANALYSIS |
|---|---|---|
| Chlorides | 1697.6 mg/L | NMX-AA-073-SCFI-2001 |
| Mercury | <0.0008 mg/L | NMX-AA-051-SCFI-2001 |
| Sodium | 376.903 mg/L | NMX-AA-051-SCFI-2001 |
| Potassium | 3.887 mg/L | NMX-AA-051-SCFI-2001 |
| Calcium | 16.662 ms/cm | NMX-AA-051-SCFI-2001 |
| Conductivity | 6.29 ms/cm | NMX-AA-093-SCFI-2001 |
| Density | 0.9989 g/mL | |

Table 2 summarizes the physicochemical characteristics of the controlled flow electrolyzed acid solution.

The shelf life of controlled flow electrolyzed acid water is one year when stored in a cool place and out of direct sunlight, since it is photo sensitive. The container should be completely and adequately sealed. Once the seal is broken, the product's life is reduced to one month, due to loss of effectivity of the electrons or protons, depending on the product.

Figure 8:
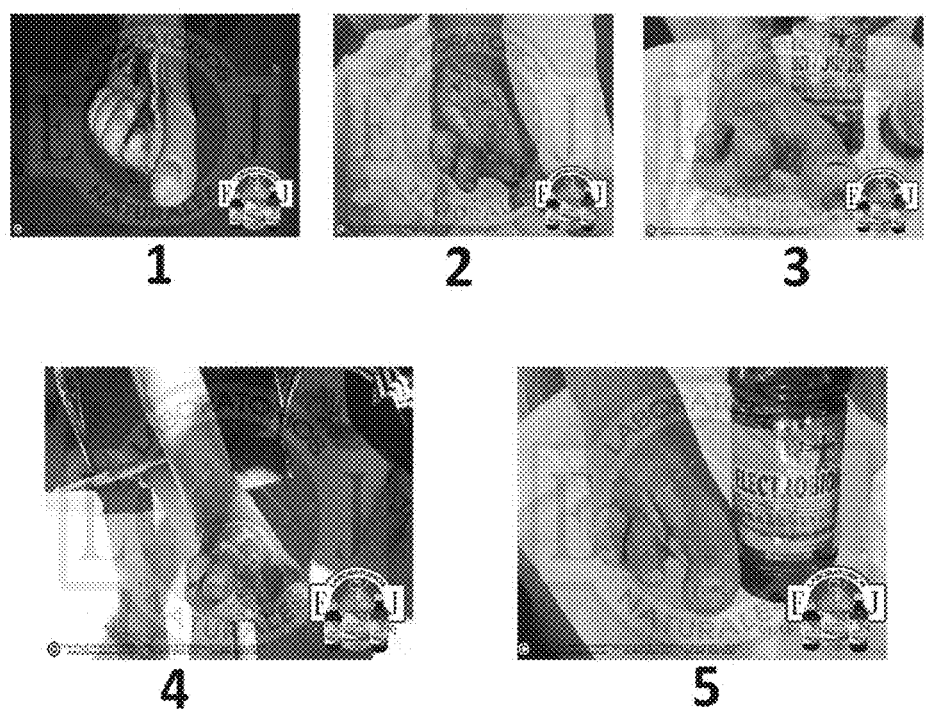
FIG. 8 is a series of photographs of the treatment of a 71 year old diabetic male patient with acid electrolyzed water produced according to an embodiment of the invention.
Figure 9:
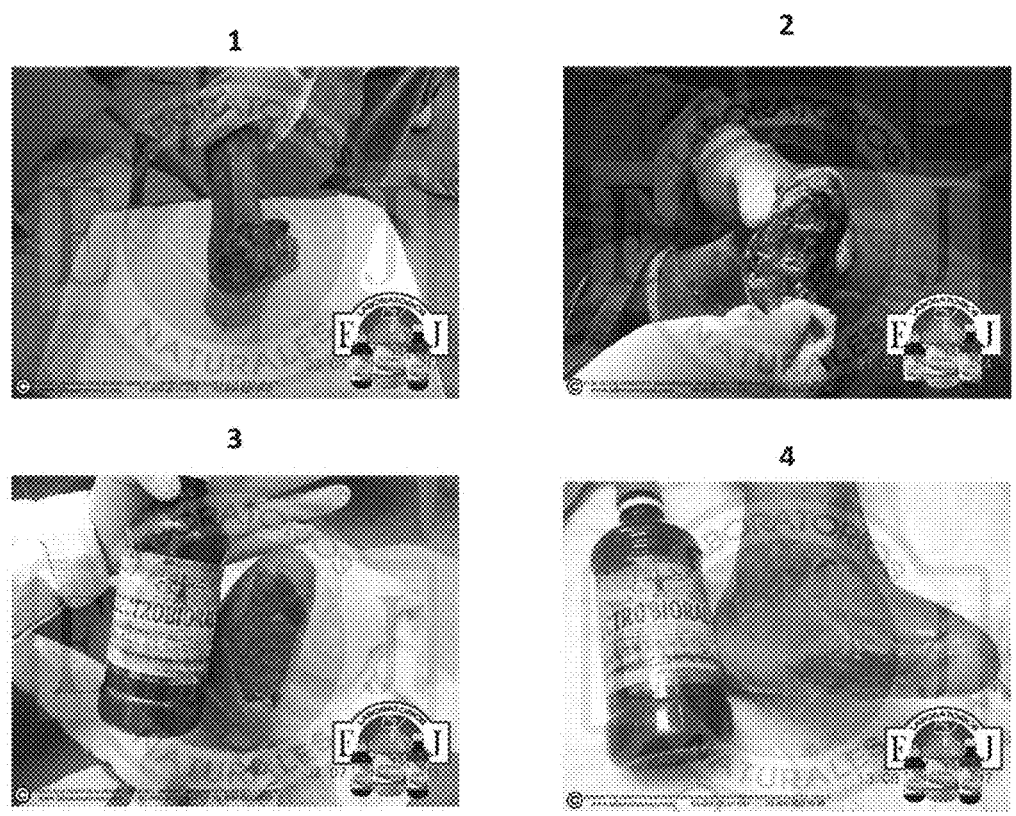
FIG. 9 is a series of photographs of the treatment of a 45 year old diabetic male patient with acid electrolyzed water produced according to an embodiment of the invention.

These characteristics (bactericide function, conductivity, oxidation, and regenerative capacity) give the controlled flow electrolyzed acid water antiseptic capabilities and the ability to treat wounds, which have been observed in the following documented cases:

- 71 year old male patient with a history of diabetes mellitus treated with insulin for 6 years, and hypertension treated with captopril for 6 years suffered a wound caused by a nail. After debriding, the resulting wound was treated with a double dose of antibiotics and applying controlled flow electrolyzed acid water every 8 hours. The results are shown in FIG. 8.
- 45 year old male patient with a clinical history of non-controlled diabetes mellitus suffered from a wound infection that was treated with antibiotics and debrided. The resulting wound was treated by applying controlled flow electrolyzed acid water every 8 hours. The results are shown in FIG. 9.

Controlled flow electrolyzed alkaline water, on the other hand, is physicochemically modified water with altered molecular structure, pH, free oxygen content, conductivity, ionic chloride content, etc. It has an impact on the human body if consumed frequently at a dosage of approximately 200 mL daily per kg of body weight. Some of the beneficial qualities of controlled flow electrolyzed water can be attributed to its characteristics that neutralize harmful waste substances in the body, restoring the acid-alkaline balance and regulating the pH of the majority of body fluids. It is also a powerful antioxidant that increases energy, since it is a rich source of stable oxygen. It produces an optimum hydration because of its content of ionic chlorides. In addition, it neutralizes acidity, inhibits excessive fermentation (in the digestive system), dissociates and maintains fats balanced, improves blood pressure, slows cellular aging, increases the assimilation of nutrients, and prevents chronic dehydration. These characteristics of controlled flow electrolyzed alkaline water make it ideal for the treatment of diseases, pains and chronic degenerative aches related to health concerns including, but not limited to cancer, diabetes, arthritis, osteoporosis, cardiac conditions, asthma, lupus, leukemia, constipation, urthicary, hemorrhoids, indigestion, headaches, and kidney, liver, and circulatory system complications.

The physicochemical characteristics and concentration of heavy metals and other constituents shown in Table 3, were measured at the National Polytechnic Institute in the National Biological Sciences school in the Central Laboratory of Instrumentation under the NOM-201-SSAA1-2002.

TABLE 3

PHYSICOCHEMICAL ANALYSIS

| PARAMETER OR CONSTITUENT | VALUE OR CONCENTRATION | MEXICAN NORM OF ANALYSIS | NOM-201-SSA1-2002 (maximum permissible limits) |
| --- | --- | --- | --- |
| Color | 1 unit (Pt—Co) | NMX-AA-045-SCFI-2001 | 15 units (Pt—Co) |
| Odor | NA | NOM-041-SSA1-95 | Odorless |
| Flavor | NA | NOM-041-SSA1-95 | Tasteless |
| Turbidity | <1 UTN | NMX-AA-038-SCFI-2001 | 5 U TN |
| Arsenic | <0.002 mg/L | NMX-AA-051-SCFI-2001 | 0.025 mg/L |
| Barium | <0.0098 mg/L | NMX-AA-051-SCFI-2001 | 0.700 mg/L |
| Boron | <0.150 mg/L | NMX-AA-051-SCFI-2001 | 0.300 mg/L |
| Cadmium | <0.0048 mg/L | NMX-AA-051-SCFI-2001 | 0.005 mg/L |
| Cyanides | <0.005 mg/L | NMX-AA-058-SCFI-2001 | 0.050 mg/L |
| Free Residual Chlorine | Not detected | NMX-AA-108-SCFI-2001 | 0.100 mg/L |
| Total Chromium | <0.0052 mg/L | NMX-AA-051-SCFI-2001 | 0.050 mg/L |
| Total Coliform Bacteria | Not detectable NMP/100mL | NMX-AA-042-SCFI-1987 | <1.1N MP/100 mL |
| Nickel | <0.012 mg/L | NMX-AA-051-SCFI-2001 | 0.020 mg/L |
| Silver | <0.007 mg/L | NMX-AA-051-SCFI-2001 | 0.100 mg/L |
| Nitrates | 1.08. mg/L | NMX-AA-79-SCFI-2001 | 10 mg/L |
| Nitrites | <0.010 mg/L | NMX-AA-99-SCFI-2001 | 0.050 mg/L |
| pH | 9.01 units | NMX-AA-008-SCFI-2000 | 6.5-8.5 Units |
| Plomo Pb | <0.0052 mg/L | NMX-AA-051-SCFI-2001 | 0.010 mg/L |
| Selenium | <0.002 mg/L | NMX-AA-051-SCFI-2001 | 0.010 mg/L |
| SAAM | <0.230 mg/L | NMX-AA-039-SCFI-2001 | 0.500 mg/L |
| Total Coliforms | Not detectable NMP/10 mL | NMX-AA-073-SCFI-2001 | <1N MP/100 mL |

PARTICULAR CONDITIONS

| PARAMETER OR CONSTITUENT | VALUE OR CONCENTRATION | MEXICAN NORM OF ANALYSIS |
| --- | --- | --- |
| Chlorides | 548.2 mg/L | NMX-AA-073-SCFI-2001 |
| Mercury | <0.0008 mg/L | NMX-AA-051-SCFI-2001 |
| Sodium | 377.774 mg/L | NMX-AA-051-SCFI-2001 |
| Potassium | 6.467 mg/L | NMX-AA-051-SCFI-2001 |
| Calcium | 1.014 mg/L | NMX-AA-051-SCFI-2001 |
| Conductivity | 2.43 ms/cm | NMX-AA-093-SCFI-2001 |
| Density | 0.9984 g/mL | |

Table 3 summarizes the physicochemical characteristics of the controlled flow electrolyzed alkaline solution.

The shelf life of controlled flow electrolyzed alkaline water is one year when stored in a cool place and out of direct sunlight, since it is photo sensitive. The container should be completely and adequately sealed. Once the seal is broken, the product's life is reduced to one month, due to loss of efficacy of the electrons or protons, depending on the product.

The controlled flow electrolyzed alkaline water can be used to treat numerous ailments, such as kidney stones. For example, a female patient suffering from kidney stones was treated with controlled flow electrolyzed alkaline water at a dosage of one liter per day, for 30 days. Ultrasound tests at the end of treatment revealed complete removal of the ailment.

With the aforementioned analyses it is determined that with the method of electrolysis by controlled flow performed with the given apparatus under the previously described production conditions, a product that complies with the required Norm for consumption is obtained. In addition, a product that meets the following parameters aids in hydration and control of internal pH: ionic chloride content greater than 500 mg/L, sodium content greater than 300 mg/L, conductivity greater than 2.0 ms/cm, pH greater than 9.0, and ORP greater than −750 mV. All of these parameters are met with the controlled flow electrolyzed alkaline water produced by the electrolyzing chamber apparatus.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An electrolysis chamber comprising:
 a) a hollow cylindrical titanium cell covered in platinum, comprising interior and exterior portions, upper and lower ends, and wherein the exterior portion comprises a lateral bolt for a cell contact;
 b) a smooth titanium cylindrical electrode covered in platinum or ruthenium, comprising two protrusion rods, each on an upper and lower end of the electrode, at least one bolt for an electrode contact, and positioned within the cylindrical titanium cell;
 c) two interior lids, each one fastened on one of the protrusion rods of the electrode, for separation and conduction of fluids, each of the interior lids including a protruding cylindrical portion having a first hole fastened to one of the protrusion rods and a second hole having a half moon shape;
 d) a high density polyethylene based separation membrane surrounding the electrode and attached to a border of each of the interior lids, maintaining fluids separated inside the electrolysis chamber and working as a medium to perform ionic exchange; and
 e) two exterior lids, one fastened on the upper end of the cell and one fastened on the lower end of the cell, wherein each exterior lid comprises a first and a second channel for entry and exit of fluids, each exterior lid being connected to a respective one of the interior lids, each of the exterior lids further including a first hole fastened to one of the protrusion rods and a second hole having a half moon shape, the first hole of each exterior lid being aligned with the first hole of each interior lid and the second hole of each exterior lid being aligned with the second hole of each interior lid,
 wherein a hermetic seal is provided at an interface between each connected interior lid and exterior lid.

2. The electrolysis chamber according to claim 1, wherein the electrode further comprises a titanium 20 caliber netting positioned over an outer surface of the electrode.

3. The electrolysis chamber according to claim 1, wherein the electrode is covered in ruthenium and works like a cathode (−).

4. The electrolysis chamber according to claim 1, wherein the electrode is covered in platinum and works like an anode (+) or a cathode (−).

5. The electrolysis chamber according to claim 1, wherein the interior and exterior lids are made of FDA GRAS grade sterile nitrile.

6. The electrolysis chamber according to claim 1, wherein the first and second channels of each exterior lid are arranged at a 180° angle relative to each other.

* * * * *